US010087467B2

(12) United States Patent
Pora et al.

(10) Patent No.: US 10,087,467 B2
(45) Date of Patent: *Oct. 2, 2018

(54) METHOD FOR THE PREPARATION AND EXTRACTION OF SQUALENE FROM MICROALGAE

(75) Inventors: Bernard Pora, Wuhan (CN); Yun Qian, Wuhan (CN); Bernard Caulier, Fretin (FR); Serge Comini, La Gorgue (FR); Philippe Looten, Lomme (FR); Laurent Segueilha, St. Andre Lez Lille (FR)

(73) Assignee: Roquette Frares, Lestrem (FR)

( * ) Notice: Subject to any disclaimer, the term of this patent is extended or adjusted under 35 U.S.C. 154(b) by 9 days.

This patent is subject to a terminal disclaimer.

(21) Appl. No.: 14/118,641

(22) PCT Filed: May 18, 2012

(86) PCT No.: PCT/EP2012/059230
§ 371 (c)(1),
(2), (4) Date: Nov. 19, 2013

(87) PCT Pub. No.: WO2012/159979
PCT Pub. Date: Nov. 29, 2012

(65) Prior Publication Data
US 2014/0088201 A1 Mar. 27, 2014

(30) Foreign Application Priority Data
May 20, 2011 (CN) .......................... 2011 1 0147052

(51) Int. Cl.
C12N 1/12 (2006.01)
C12P 5/02 (2006.01)
C12P 5/00 (2006.01)

(52) U.S. Cl.
CPC ............... *C12P 5/026* (2013.01); *C12N 1/12* (2013.01); *C12P 5/007* (2013.01); *C12P 5/02* (2013.01)

(58) Field of Classification Search
None
See application file for complete search history.

(56) References Cited

U.S. PATENT DOCUMENTS

| | | | |
|---|---|---|---|
| 5,130,242 A * | 7/1992 | Barclay | A23K 1/008 426/49 |
| 6,248,779 B1 | 6/2001 | Shimizu et al. | |
| 2014/0073037 A1 | 3/2014 | Patinier | |
| 2014/0113015 A1 | 4/2014 | Pora et al. | |
| 2015/0140030 A1 | 5/2015 | Looten et al. | |
| 2015/0159116 A1 | 6/2015 | Patinier et al. | |

FOREIGN PATENT DOCUMENTS

| | | |
|---|---|---|
| EP | 2 650 356 | 10/2013 |
| WO | WO 2007/039149 | 4/2007 |
| WO | WO 2010/023551 | 3/2010 |
| WO | WO 2012/077799 | 6/2012 |
| WO | WO 2012/159980 | 11/2012 |
| WO | WO 2012/164211 | 12/2012 |
| WO | WO 2013/156720 | 10/2013 |
| WO | WO 2013/178936 | 12/2013 |

OTHER PUBLICATIONS

Hayashi et al., Bioscience, Biotechnology, and Biochemistry, vol. 71, Issue 1, 2007, pp. 222-225.*
Yokoyama et al., Mycoscience (2007) 48:199-211.*
Chen, G. et al. "Optimization of nitrogen source for enhanced production of squalene from thraustochytrid *Aurantiochytrium* sp" *New Biotechnology*, Sep. 30, 2010, pp. 382-389, vol. 27, No. 4.
Fan, K. et al. "Enhanced production of squalene in the thraustochytrid *Aurantiochytrium mangrovei* by medium optimization and treatment with terbinafine" *World Journal of Microbiology and Biotechnology*, Jan. 8, 2010, pp. 1303-1309, vol. 26, No. 7.
Yue, C.-J, et al. "Impact of methyl jasmonate on squalene biosynthesis in microalga *Schizochytrium mangrovei*" *Process Biochemistry*, Aug. 1, 2009, pp. 923-927, vol. 44, No. 8.
Kaya, K. et al. "Thraustochytrid *Aurantiochytrium* sp. 18W-13a Accummulates High Amounts of Squalene" *Bioscience Biotechnology Biochemistry*, Nov. 2011, pp. 2246-2248, vol. 75, No. 11.
Nakazawa, A. et al. "Optimization of culture conditions of the thraustochytrid, *Aurantiochytrium* sp. strain 18W-13a for squalene production" *Bioresource Technology*, Apr. 2012, pp. 287-291, vol. 109.
Written Opinion in International Application No. PCT/EP2012/059230, dated Jul. 10, 2012, pp. 1-9.
Nakazawa, A. et al. "Optimization of culture conditions of thraustochytrid, *Aurantiochytrium* sp. strain 18W-13a for squalene production" *The 1st Asia Oceania Algae Innovation Summit*, Dec. 13, 2010, pp. 1-2.
Tsui, C. et al. "Labyrinthulomycetes phylogeny and its implications for the evolutionary loss of chloroplasts and gain of ectoplasmic gliding" *Molecular Phylogenetics and Evolution*, Jan. 1, 2009, pp. 129-140, vol. 50, No. 1.
Database GenBank [Online] Accession No. DQ367050.1, "*Schizochytrium* sp. ATCC 20888 18S ribosomal RNA, partial sequence" Sep. 30, 2006, pp. 1-2, XP-002681840.
Qian, L. et al. "Screening and Characterization of Squalene-Producing Thraustochytrids from Hong Kong Mangroves" *Journal of Agricultural and Food Chemistry*, May 10, 2009, pp. 4267-4272, vol. 57, No. 10.
Jiang, Y. et al. "Fatty Acid Composition and Squalene Content of the Marine Microalga *Schizochytrium mangrovei*" *Journal of Agricultural and Food Chemistry*, Mar. 10, 2004, pp. 1196-1200, vol. 52, No. 5.

(Continued)

*Primary Examiner* — Irene Marx

(57) ABSTRACT

The invention relates to a method for the production of squalene from microalgae belonging to the family of *Thraustochytriales* sp., preferably at concentrations of between 2 and 12 g per 100 g of dry biomass. The method is characterized in that it comprises steps consisting in: culturing microalgae belonging to the family of *Thraustochytriales* sp. at a temperature of between 25 and 35° C., preferably between 28 and 32° C., and more preferably of the order of 30° C.; and adding between 1 and 1000 µg of vitamin B12 per liter of culture medium to said culture medium.

12 Claims, No Drawings

(56) References Cited

OTHER PUBLICATIONS

Written Opinion in International Application No. PCT/EP2012/059231, dated Sep. 4, 2012, pp. 1-8.
Currently pending claims of U.S. Appl. No. 14/118,605, 2016, pp. 1-2.
Currently pending claims of U.S. Appl. No. 14/118,674, 2015, pp. 1-2.
Currently pending claims of U.S. Appl. No. 14/394,813, 2015, pp. 1-3.
Allowed claims of U.S. Appl. No. 14/403,611, 2015, pp. 1-2.

* cited by examiner

METHOD FOR THE PREPARATION AND EXTRACTION OF SQUALENE FROM MICROALGAE

CROSS-REFERENCE TO RELATED APPLICATION

This application is the U.S. national stage application of International Patent Application No. PCT/EP2012/059230, filed May 18, 2012.

The present invention relates to a process for the optimized production of squalene by fermentation from microalgae of the *Thraustochytriales* sp. family.

For the purposes of the invention, the expression "microalgae of the *Thraustochytriales* sp. family" is intended to mean microalgae belonging to the *Schizochytrium* sp., *Aurantiochytrium* sp. and *Thraustochytrium* sp. species.

Squalene is a triterpene, an isoprenoid comprising 30 carbon atoms and 50 hydrogen atoms, of the formula: 2,6,10,15,19,23-hexamethyl-2,6,10,14,18,22-tetracosa-hexene.

It is a lipid that is naturally produced by all higher organisms, including human beings (found in sebum). Squalene is in fact an essential intermediate in the biosynthesis of cholesterol, steroid hormones and vitamin D (an enzyme of the cholesterol metabolic pathways, squalene monooxygenase, will, by oxidizing one of the ends of the squalene molecule, induce cyclization thereof and result in lanosterol, which will be converted to cholesterol and to other steroids).

Industrially, squalene is especially used in the food sector, the cosmetics field and the pharmaceutical field.

As a food supplement, squalene is usually formulated as capsules or as oils.

In the cosmetics field, this molecule can be used as an antioxidant, an antistatic and an emollient in moisturizing creams, penetrating the skin rapidly without leaving fatty traces or sensations, and mixing well with other oils and vitamins.

In this field, it should be noted that, given the very high instability of squalene (6 unsaturations), it is the saturated form squalane (obtained by hydrogenation), a better antioxidant than squalene, which is found on the market, generally with a very high level of purity (99%).

Toxicological studies have shown that, at the concentrations used in cosmetics, squalene and squalane do not exhibit any toxicity, and are not irritant or sensitizing to human skin.

In the pharmaceutical field, squalene is used as adjuvants for vaccines.

These adjuvants are substances which stimulate the immune system and increase the response to the vaccine.

Squalene has been used in the form of an emulsion added to the vaccinating substances, in order to make the vaccine more immunogenic, since 1997 in an influenza vaccine (Fluad, from the company Chiron, against seasonal influenza) at approximately 10 mg of squalene per dose.

Like all vaccines containing squalene, these emulsions have a milky white appearance.

Squalene is also used as a vaccine adjuvant, in particular in experimental vaccines, antimalarial substances and influenza vaccine targeting the emerging viruses H5N1, and then in 2009 H1N1, as:

a patented constituent of the AS03 adjuvant system used by GlaxoSmithKline in the Pandemrix and Arepanrix vaccine against the 2009 influenza pandemic, and a patented constituent of the MF59 adjuvant system used by Novartis.

Squalene has also been added to influenza vaccines to stimulate the immune response of the human body through the production of memory CD4 cells.

It is the first oil-in-water adjuvant for influenza vaccines to have been marketed in combination with the seasonal influenza virus antigens.

The level of purity of the squalene is essential in this application field.

Indeed, if it is taken orally, squalene is considered to be completely safe; however, the injectable route is the subject of controversy.

Indeed, in the medical field, the risk of harm for a human recipient may be increased in situations where squalene is contaminated with impurities, since, by definition, this adjuvant can also induce a strong immune response against its own impurities.

It is therefore essential to have high-quality squalene free of impurities (traces of metals, in particular of mercury, and of other toxins).

A certain number of pathways for producing squalene are proposed in the literature.

It is a compound which is often found stored in the livers of cartilaginous fish such as deep-sea sharks (hence its name).

It is therefore one of the reasons why they are overfished, the sharks already being hunted for their fins. Shark livers are now sold to produce gel capsules described as "good for the health".

However, while the squalene marketed is thus mainly extracted from shark livers, it is not free of health problems.

This is because sharks can be infected with pathogens that can produce substances harmful to human beings. In addition, the shark liver, which is the organism's elimination and purification organ, may contain toxins such as carchatoxin which is harmful to human beings.

These environmental concerns (large decrease in shark numbers) and health concerns (fish livers also store toxins that are of concern with regard to health) have prompted its extraction from plants.

It is thus possible to isolate it from olive oil, palm oil, and other oils from cereals or originating from amaranth, seeds, rice bran or wheat germ.

However, the major drawback in this case is that the squalene is extracted in very small amounts, of about from 0.1% to 0.7% by weight.

As a first alternative to these processes of extraction from shark livers or from plants, often made expensive by the implementation of substantial enrichment and purification processes, the first processes for producing squalene from microorganisms—natural yeasts or recombinant yeasts, in particular the *Saccharomyces* type—have been proposed.

Thus, *Saccharomyces cerevisiae* is known for its ability to produce squalene, however in very small amounts: of about 0.041 mg/g of biomass (Bhattacharjee, P. et al., 2001, in *World J. Microb. Biotechnol.*, 17, pp. 811-816).

Work has therefore been carried out on the optimization of these production capacities, by means of genetic recombination.

The recombinant yeasts which produce squalene thus have the advantages:

of benefiting from the same GRAS (Generally Regarded As Safe) status as the host cell, of being free of pathogens, prions or toxins, just like the host cell, and of having already been used in the vaccine field (such as those yeasts which express vectors containing hepatitis B antigens).

However, as presented by patent application WO 2010/023551 for the medical field (production of squalene with a purity greater than 97% as a vaccine adjuvant), this first alternative is industrializable only if it is possible to have recombinant yeasts hyperproducing squalene (at more than 15% by weight of dry cells).

As it happens, obtaining these recombinant cells requires the implementation of numerous laborious, lengthy and complex metabolic engineering steps, using molecular biology tools, resulting in the stimulation of the squalene biosynthesis pathways and in the inhibition of the squalene catabolism pathways.

Indeed, as WO 2010/023551 states, there are many genes involved in squalene biosynthesis, including mevalonate kinase, phosphomevalonate kinase, pyrophosphomevalonate decarboxylase, isopentenyl pyrophosphate isomerase, HMGR (3-hydroxy-3-methylglutaryl-CoA reductase) and squalene synthetase.

For the catabolism pathways, genes encode numerous enzymes involved in the conversion of squalene to ergosterol, including squalene epoxidase (ERG1), lanosterol synthetase, C14-dimethylase, d14-reductase, C4-methyloxidase, C4-decarboxylase (ERG26), 3-ketoreductase, C24-methyltransferase, C8-isomerase, C5-desaturase, d22-desaturase and d24-reductase.

Moreover, other catabolic enzymes must also be taken into consideration: LEU2 ([beta]-isopropyl malate dehydrogenase), oxidosqualene cyclase, zymosterol-24-methyltransferase and ergosta-5,7,24(28)-trienol-22-dehydrogenase.

As a second alternative to the processes of extraction from shark livers or from plants, promising processes for producing squalene from microalgae of the *Thraustochytriales* family (comprising the genera *Thraustochytrium*, *Aurantiochytrium* and *Schizochytrium*), more particularly *Schizochytrium mangrovei* or *Schizochytrium limacinum*, have been proposed.

These microalgae produce squalene under heterotrophic conditions (absence of light; provision of glucose as a carbon source), and can therefore be easily manipulated by those skilled in the art in the field of microorganism fermentation.

These processes therefore offer, by means of controlled fermentation conditions, qualities of squalene of which the purification can be easily carried out to meet food, cosmetic and medical needs.

In these microalgae of the *Thraustochytriales* family, squalene is, however, the coproduct of other lipid compounds of interest, such as docosahexaenoic acid (or DHA), a polyunsaturated fatty acid of the ω3 family.

It thus appears that squalene is specially described as one of the components of the unsaponifiable fraction of commercial DHA oils (along with carotenoids and sterols).

By way of comparison, the *Schizochytrium mangrovei* FB1 strain produces DHA in a proportion of 6.2% by dry weight of cells, for 0.017% of squalene.

As a result, these microorganisms which naturally produce squalene do so in small amounts:
of about 0.1 mg/g of biomass, for Thraustochytrid ACEM 6063 (cf. Lewis et al., in *Mar. Biotechnol.*, 2001, 439-447), and
of about 0.162 mg/g of biomass, for *Schizochytrium mangrovei* FB1 (cf. Jiang et al., in *J. Agric. Food Chem.*, 2004, 52, pp. 1196-1200).

In order to increase production, it therefore appears to be essential to optimize the fermentation conditions.

In the article by Qian Li et al., in *J. Agric. Food Chem.*, 2009, 57, 4267-4272, it is specified that squalene is a key intermediate of sterol biosynthesis, and that the first step of the conversion of squalene to sterols is catalyzation by an oxygen-dependent squalene epoxidase.

Conditions rich in dissolved oxygen are therefore to be prohibited if it is desired, on the contrary, to accumulate intracellular squalene.

Thus, culturing Thraustochytrid ACEM 6063 at a low dissolved oxygen level (0 to 5% saturation) makes it possible to accumulate more than 1 mg/g of squalene, whereas growth at a higher dissolved oxygen level (40% to 60%) makes it possible to achieve only 0.01 mg/g of squalene.

Likewise, culturing at a temperature of 15° C. puts the production of squalene by Thraustochytrid ACEM 6063 at 1.2 mg/g, whereas it is only 0.7 mg/g at 20° C. (cf. Lewis et al., in *Mar. Biotechnol.*, 2001, 3, 439-447).

In the article by G. Chen et al., in *New Biotechnology*, 2010, 27-4, pp. 382-389, it is stated that *Schizochytrium* mainly produces DHA, by means of the polyketide synthase (PKS) pathway, whereas squalene is instead synthesized by means of the cholesterol biosynthesis pathway, which means that the nutritional needs of thraustochytrids for these two compounds are distinct.

The object of their work was therefore to systematically investigate the effect of various sources of nitrogen in the production of squalene.

G. Chen et al. thus found that *Schizochytrium* could grow rapidly and accumulate "high" amounts of squalene in a culture medium containing a mixture of nitrogenous sources consisting of monosodium glutamate, yeast extract and tryptone.

Despite that, this "high" production of squalene is entirely relative.

If, while the authors succeed in significantly increasing the squalene content and the yield by 26.3% and 10.1%, respectively, relative to the values of the basic medium, these optimized conditions in fact produce a squalene content of 0.72 mg/g and a titer of 5.90 mgl/l.

With this same objective of optimizing squalene production, K. W. Fan et al., in World J. Microbiol. Biotechnol., 2010, 26-3, pp. 1303-1309, used an inhibitor of squalene monooxygenase (a key enzyme in sterol biosynthesis): terbinafine hydroxychloride.

It is known that the squalene content and yield are linked to the age of a microorganism culture.

The more the cell culture ages, the less it accumulates squalene; in fact, the more it consumes said squalene in the sterol biosynthesis pathway.

Terbinafine therefore acts by preventing this consumption of squalene toward the sterol pathway and therefore makes it possible to stimulate the intracellular accumulation of squalene by up to 36% to 40% relative to the control.

However, the highest squalene production obtained with the *Aurantiochytrium mangrovei* FB3 strain used in this study, even though much higher than that described for *S. cerevisiae* (0.041 mg/g of biomass), or even that described for *Torulaspora debrueckii* (0.24 mg/g of biomass), is only 0.53 mg/g of biomass.

Moreover, while this diversion of the metabolic pathways allows the squalene a relatively greater amount, it risks weakening the cells by accordingly limiting the production of sterols essential for the production of the lipid membranes of these same cells.

Among the highest squalene production results using microalgae that are reported in the literature, the article by C-J Yue and Y. Jiang, *Process Biochemistry*, 2009, 44, 923-927, indicates a maximum squalene content of 1.17±0.6 mg/g of biomass of *Schizochytrium mangrovei*, which uses methyl jasmonate to modulate the metabolic pathways of squalene synthesis by acting directly on squalene synthetase, a key enzyme of said metabolic pathways.

Thus, despite all the efforts made, these values are much lower than the reference values for olive oil (of about 4.24 mg/g) and are far from the values required on the industrial scale.

Concerned with developing a process of production which is much more effective and much less expensive than those described in the prior art, the applicant company has developed its own research on the optimization of the fermentation conditions for microalgae of the *Thraustochytriales* sp. family.

The invention therefore relates to a process for obtaining squalene on the scale of one gram for 100 grams of dry biomass, i.e., up to 1000 times more than what is usually described in the literature in this field.

The invention also relates to a process for the extraction and purification of squalene from the resulting fermentation medium.

Production of Squalene by Fermentation of *Schizochytrium*

It is first of all to the applicant company's credit to have found that, among all the parameters for controlling fermentation, two of them make it possible on their own to considerably increase the squalene production level in these microalgae.

These two key parameters are the temperature of the culture medium, and the addition of vitamins, more precisely vitamins B1 and B6 and especially vitamin B12.

The present invention therefore relates to a process for the production of squalene by microalgae belonging to the *Thraustochytriales* sp. family, characterized in that it comprises the following steps:
  culturing microalgae belonging to the *Thraustochytriales* sp. family at a temperature of between 25 and 35° C., preferably between 28 and 32° C., more preferably of about 30° C., and
  adding to the culture medium 1 to 1000 µg of vitamin B12 per liter of culture medium.

Preferentially, as will be indicated hereinafter, the applicant recommends adding:
  0.1 mg to 200 mg of vitamin B1 per liter of culture medium, and/or
  0.1 mg to 200 mg of vitamin B6 per liter of culture medium.

Of course, the process may comprise a step of recovering the squalene-rich biomass and/or a step of recovering or extracting the squalene.

More particularly, the following commercially available strains have been tested:
  *Schizochytrium* sp. referenced ATCC 20888, and
  *Aurantiochytrium* sp. referenced ATCC PRA 276.

Moreover, the applicant company also has its own production strain, a *Schizochytrium* sp. deposited on Apr. 14, 2011, in France with the Collection Nationale de Cultures de Microorganismes [National Collection of Microorganism Cultures] of the Institut Pasteur under No. CNCM I-4469 and also deposited in China with the CHINA CENTER FOR TYPE CULTURE COLLECTION of the University of Wuhan, Wuhan 430072, P. R. China, under No. M 209118.

A strain of *Schizochytrium* mangrovei has also been tested as a control, as will be exemplified hereinafter.

In particular, the process according to the present invention makes it possible to obtain squalene contents greater than or equal to 2 g for 100 g of dry biomass, preferably between 2 and 12 g for 100 g of dry biomass. In particular, the quantification of squalene produced can be carried out according to the method detailed in the experimental section.

In the process in accordance with the invention, the first essential characteristic is therefore the choice of the temperature at which both the culturing of the microalgae and the squalene production thereof will be carried out.

The temperature is thus chosen between 25 and 35° C., preferably between 28 and 32° C., more preferably about 30° C.

The applicant company has therefore overcome a first technical preconception which requires that the culturing of these microalgae should not exceed 25° C.

Indeed, in most of the articles cited above for the production of squalene in *Thraustochytriales*, the production temperatures were set on the basis of the growth temperatures of the microalgae studied, i.e., 15° C., 22° C. or 25° C.

According to the process of the invention, the applicant company recommends, on the contrary, culturing these microalgae at 28 and 32° C., since it has been able to note that:
  while the squalene concentration produced by the cell biomass increases with the temperature up to 33° C., beyond 30° C. the amount of biomass is significantly reduced, thus limiting the squalene titer, and
  at a temperature of 25° C., the squalene concentrations are undetectable or very low.

This temperature range is therefore a compromise between the temperature for optimum culturing of the microalgae, and that for effective production of squalene.

The temperature of at most 25° C. is not therefore, contrary to what is commonly used in the prior art, the temperature which best promotes squalene production.

In the process in accordance with the invention, the second essential characteristic is the amount of vitamin B12 with which the *Schizochytrium* culture medium is provided for the production of squalene, i.e., in a proportion of from 1 to 1000 µg of vitamin B12 per liter of culture medium.

Preferably, this addition of vitamin B12 can be supplemented with:
  0.1 mg to 200 mg of vitamin B1 per liter of culture medium, and/or
  0.1 mg to 200 mg of vitamin B6 per liter of culture medium.

In the literature relating to the production of squalene by the microalgae mentioned above, the role of vitamins is not considered. The provision of vitamins is conventionally carried out by means of the addition of yeast extracts.

It is in fact well known to those skilled in the art that these vitamins are naturally present in yeast extracts in a proportion of:
  50 to 120 mg/kg of vitamin B1 (thiamine),
  40 to 80 mg/kg of vitamin B6 (pyridoxine), and
  1 to 5.5 µg/kg of vitamin B12 (cyanocobalamin), to mention just these three vitamins B.

However, the provision of yeast extracts introduced into the culture media is only from 1 to 2 g for 100 ml of culture medium (cf. the scientific articles listed above), which corresponds to extremely low vitamin doses (for example, the provision of vitamin B12 by yeast extracts corresponds to 0.07 µg/l).

Be that as it may, this set of documents neither describes nor suggests controlling the content of vitamin B1, B6 or B12 for the production of squalene in microalgae.

Without being bound by any theory, the applicant company has found that the predominant role of vitamin B12 in the production of squalene (as will be exemplified hereinafter) would suggest its involvement as a cofactor of some of the key enzymes involved in squalene biosynthesis.

As for vitamin B1, it would stimulate the leucine degradation pathway, which would increase the intracellular amount of squalene precursors, and vitamin B6, by modifying the action of cytochromes, would prevent squalene degradation.

The applicant company has therefore found that the provision of vitamin B12 is, with the temperature brought to 28 and 30° C., the key to considerably increasing the production of squalene (on the scale of 1 g/100 g of dry biomass) and the provision of vitamins B1 and B6 in fact makes it possible especially to increase squalene productivity, as will be demonstrated hereinafter.

Another characteristic of the process in accordance with the invention is that the addition of the vitamins can be carried out throughout the fermentation process, or during some of its steps, and not only in the production phase.

However, the provision of between 1 and 1000 µg/l of vitamin B12 over the whole of the fermentation process must be adhered to.

Conventionally, in the literature relating to the work for optimizing the conditions for squalene production by microalgae carried out in the laboratory, the fermentation is performed on the basis of a conventional microbial inoculation and production chain, and it is the production conditions which are generally worked upon the most.

The production of squalene from *Thraustochytrium* in fact requires three successive steps: start from an isolated colony on an agar dish, preculture to revive the strain and, finally, culture (=production) per se.

For example, the article by G. Chen mentioned above describes the process which comprises the following successive steps:
- start from a strain maintained on agar nutritive medium comprising glucose, monosodium glutamate, yeast extract and various trace elements,
- prepare a preculture in Erlenmeyer flasks on an orbital shaker, at a pH of 6, at a temperature of 25° C. in order to obtain a revived biomass, and
- inoculate another series of production Erlenmeyer flasks with the same culture medium as that used in the preculture, with about 0.5% (v/v) of the biomass obtained in the previous step, and maintain the temperature at 25° C.

As it happens, as can be read in said article (but this proves to be true for the other articles in the field), it is at the level of the latter culturing step that specialists act in order to optimize the fermentation conditions.

In other words, the prior art optimization studies consist of varying one or more components of the production medium in order to study the influence thereof on the production of squalene.

However, as will be developed hereinafter, the applicant company recommends, on the contrary, controlling the fermentation conditions right from the first steps, even if they prove to be more complex to implement on an industrial scale.

On this scale, in fact, the inoculation chain can be composed of several preculture steps in series before the actual production step.

One preferred embodiment of the process in accordance with the invention can therefore consist of the succession of the following steps:
- first, preculturing the microalga of the *Thraustochytriales* family for 24 to 36 hours in Erlenmeyer flasks, at a temperature of 28° C., from an isolated colony on an agar dish,
- second, preculturing for 24 to 36 hours in Erlenmeyer flasks, at a temperature of 28° C., with an inoculum of 1% (v/v) resulting from the first preculturing, and
- culturing for 60 to 150 hours at 30° C., in a fermenter conditioned so as to observe an oxygen transfer of at most 45 mmol/l/hour, with an inoculum of 0.5% to 2% (v/v) resulting from the second preculturing.

In this chaining, depending on the operating conditions, as will be exemplified hereinafter, the addition of the vitamins can be carried out in a single preculturing step, in two preculturing steps or throughout the culturing chain.

As will be demonstrated hereinafter, the addition of vitamins in a single preculturing step already makes it possible to obtain remarkable results, the optimized mode requiring an addition at all the steps implemented.

The carbon source required for the growth of the microalgae is preferably glucose.

The applicant company therefore recommends controlling the addition of glucose so as to provide a total amount of glucose of from 15% to 22.5% by weight.

Be that as it may, as will be exemplified hereinafter with the *Schizochytrium* strains selected, it is preferred to work at a non-zero residual glucose content, at most equal to 8% by weight.

With regard to the nature of the nitrogen source, the applicant company has found that it is possible to select it from the group consisting of yeast extracts, urea, sodium glutamate and ammonium sulfate, alone or in combination.

It is possible to prefer to the yeast extracts conventionally used in the prior art processes, urea supplemented with a vitamin cocktail, such as the BME cocktail sold by Sigma, used at 5 ml/l.

Likewise, it is possible to totally or partially replace the urea with sodium glutamate, or to use a mixture of sodium glutamate and ammonium sulfate.

The applicant company especially recommends not using a source of nitrogen in nitric forms.

With regard to the pH of the culture medium, as will be exemplified hereinafter, it will be maintained between 5.5 and 6.5, preferentially fixed at a value of 6.

The pH can be regulated by any means known to those skilled in the art, for example by adding 2 N sulfuric acid, and then with 8 N sodium hydroxide.

Finally, the dissolved oxygen content can be regulated at a value between 20% and 0%, preferably maintained at 5% for an initial period of 24 or 48 hours, preferably 36 hours, before being left at 0%.

With regard to the oxygen transfer, it will be regulated by any means known, moreover, to those skilled in the art, so as not to exceed 45 mmol/l/hour.

As will be exemplified hereinafter, the biomass obtained under these operating conditions, at the end of fermentation, is more than 50 g/l, preferably between 50 and 100 g/l, about 80 g/l.

The squalene content is, for its part, more than 1 g for 100 g of dry biomass, preferably between 2 and 15 g for 100 g of dry biomass, even more preferentially between 5 and 10 g for 100 g of dry biomass.

Extraction and Purification of the Squalene from the Fermentation Medium

The biomass is recovered from the fermentation medium by any method known to those skilled in the art; for example the biomass can be removed from the fermenter and simply concentrated by microfiltration or centrifugation, or washed via a succession of concentrations and dilutions with an aqueous solution.

The rupturing of the cells in order to extract the lipid content can be carried out via various routes, among which are mechanical, chemical or enzymatic routes.

The oil is extracted from the cell lysate with hexane/ethanol in several successive extractions.

The hexane fraction is separated and then the hexane is evaporated off so as to isolate the crude oil.

The present invention finally relates to the use of the squalene produced by means of any of the processes of the present invention in the preparation of compositions intended for the medical field, the cosmetics field and the food sector. Thus, it relates to a method for the preparation of compositions intended for the medical field, the cosmetics field and the food sector, comprising the production of squalene by any of the processes of the present invention, and then the preparation of compositions intended for the medical field, the cosmetics field and the food sector.

The invention will be understood more clearly by means of the examples which follow, which are intended to be illustrative and nonlimiting.

EXAMPLE 1: STUDY OF THE ADDITION OF VITAMINS B1, B6 AND B12 AND THE INFLUENCE OF TEMPERATURE ON SQUALENE PRODUCTION

Preculture and Culture Media

The fermentation of the microalgae was carried out in two prior successive preculturing phases before the actual culturing/production phase.

For this experiment, the vitamins were added to the first preculture medium, but addition thereof to the second preculture medium and in production was optional.

The preculture media therefore had the composition given in Tables I and II:

TABLE I

| Medium of the first preculture | % |
| --- | --- |
| Glucose | 3 |
| Yeast extracts | 0.4 |
| Sodium salt of glutamic acid | 6.42 |
| NaCl | 1.25 |
| $MgSO_4$ | 0.4 |
| KCl | 0.05 |
| $CaCl_2$ | 0.01 |
| $NaHCO_3$ | 0.05 |
| $KH_2PO_4$ | 0.4 |
| Vitamin mixture | 0.14 |
| Trace elements | 0.8 |

TABLE II

| Medium of the second preculture | % |
| --- | --- |
| Glucose | 8.57 |
| Sodium salt of glutamic acid | 6.42 |
| Yeast extracts | 0.64 |
| NaCl | 2 |
| $KH_2PO_4$ | 0.64 |

TABLE II-continued

| Medium of the second preculture | % |
| --- | --- |
| $MgSO_4$ | 2.29 |
| $CaCl_2$ | 0.03 |
| $NaHCO_3$ | 0.03 |
| $Na_2SO_4$ | 0.03 |
| Addition of the vitamin mixture | 0.14 |
| Trace elements | 0.2 |

Generally, Clerol FBA 3107 antifoam was used at 1 ml/l.

Optionally, 50 mg/l of penicillin G sodium salt was used in order to prevent the growth of contaminating bacteria.

The glucose was sterilized with $KH_2PO_4$ separately from the rest of the medium since the formation of a precipitate (Magnesium-Ammonium-Phosphate) was thus avoided.

The vitamin mixture and the trace elements were added after sterilizing filtration.

The composition of the culture/production medium is given by Table III.

TABLE III

| | % |
| --- | --- |
| Glucose addition at T0 | 7.5 |
| Urea | 1 |
| Yeast extracts | 1.2 |
| NaCl | 0.25 |
| $KH_2PO_4$ | 0.96 |
| $MgSO_4$ | 1.2 |
| $CaCl_2$ | 0.12 |
| $NaHCO_3$ | 0.12 |
| KCl | 0.08 |
| If addition of the vitamin mixture | 0.4 |
| Trace elements | 0.56 |

The composition of the vitamin mixtures and of the trace elements is given in Tables IV and V:

TABLE IV

| Vitamin mixture | g/l |
| --- | --- |
| B1 | 45 |
| B6 | 45 |
| B12 | 0.25 |

TABLE V

| Trace elements | g/l |
| --- | --- |
| $MnCl_2 \cdot 2H_2O$ | 8.60 |
| $CoCl_2 \cdot 6H_2O$ | 0.2 |
| $NiSO_4 \cdot 6H_2O$ | 7.50 |
| $Na_2MoO_4 \cdot 2H_2O$ | 0.15 |
| $ZnSO_4 \cdot 7H_2O$ | 5.70 |
| $CuSO_4 \cdot 5H_2O$ | 6.50 |
| $FeSO_4 \cdot 7H_2O$ | 32.00 |
| $ZnCl_2$ | 1.50 |

Performing the Fermentation

The first preculturing was carried out in 500 ml baffled Erlenmeyer flasks to which a drop of Clerol FBA 3107 antifoam sold by Cognis GmbH Düsseldorf was added.

The culture medium was filtered after complete dissolution of its constituents, optionally supplemented with penicillin G sodium salt in a proportion of 0.25 mg/l.

The inoculation was carried out by taking colonies of microalgae cultured in a Petri dish (in a proportion of one 10 µl loop).

The incubation lasted 24 to 36 hours, at a temperature of 28° C., with shaking at 100 rpm (on an orbital shaker).

Since the biomass settles out (or adheres to the wall), care was taken to sample 3 to 5 ml after having shaken the Erlenmeyer flasks well.

For the second preculturing, 2 l baffled Erlenmeyer flasks fitted with tubing were used.

A drop of antifoam and the yeast extract were added to 100 ml of water.

All of the constituents of the medium were filtered after dissolution in 300 ml of demineralized water. It was possible to optionally add penicillin G sodium salt and beforehand to the Erlenmeyer flask a drop of antifoam before its sterilization.

The inoculation was then carried out with 3 to 5 ml of the first preculture.

The incubation was carried out at 28° C. for a further 24 to 36 hours, with shaking at 100 rpm.

The actual culturing was carried out in the following way in a 20 l reactor:
sterilization of a part of the medium in the reactor, and sterilization of the other part separately so as to prevent the formation of a precipitate,
inoculation carried out using the biomass produced at the end of the second preculturing, in a proportion of 0.5% v/v of the culture medium,
culture maintained at 30° C.,
oxygen transfer rate fixed at 35-40 mmol/l/h,
aeration of 0.2 to 0.3 VVM,
initial pH>5.5, and
feeding with glucose as soon as the concentration is >20%, so as to maintain a glucose concentration of between 15 and 70 g/l.

The following table gives the results obtained with the *Schizochytrium* sp. of the applicant company.

This table gives:
the effect of the temperature on the production of squalene (addition of vitamins only in the two preculturing operations: tests "B" and "C"), and
the effect of the addition of vitamins B1, B6 and B12 in the preculturing and production steps (tests "D" and "E"), compared with a standard without the addition of vitamins (test "A").

A control without supplementary addition of vitamins at 25° C. was also carried out.

TABLE V

| Tests | A | B | C | D | E |
|---|---|---|---|---|---|
| Addition of vitamins B1, B6 and B12 in preculturing operations | No | Yes | Yes | Yes | Yes |
| Addition of vitamins B1, B6 and B12 in production | No | No | No | Yes | Yes |
| Preculturing temperature (° C.) | 25 | 28 | 28 | 28 | 28 |
| Culturing temperature (° C.) | 25 | 25 | 30 | 25 | 30 |
| Squalene titer at the end of culturing (g/l) | Non-detectable (ND) | 0.7 | 0.5 | 2.3 | 4.4 |
| Biomass (g/l) | 35 | 64 | 53 | 70 | 54 |
| % of squalene to dry biomass | ND | 1.1 | 0.9 | 3.3 | 8.2 |

It should be noted that the control "A", under the conventional conditions of the literature, did not enable the production of detectable amounts of squalene for the microalgal strain tested.

For tests "B" and "C":

A preculturing temperature of 28° C. and the presence of vitamins B1, B6 and B12 in the preculturing operations already made it possible to provide a squalene production of about 1 g for 100 g of biomass (test "B"), i.e., approximately 1000 times more than what is described in the literature (for example for the production of squalene by Thraustochytrid ACEM 6063 or *S. mangrovei* FB1).

For tests "D" and "E":

The effect of the temperature coupled with the addition of vitamins at all the culturing steps (the 2 preculturing operations and the production) is remarkable. Test "D" enabled the production of 3.3 g of squalene for 100 g of biomass when the temperature was left at 25° C., which increased for test "E" to 8.2 g/l when the temperature was brought to 30° C.

The performing of the fermentation conditions at temperatures above 25° C., coupled with the sizeable addition of vitamins B1, B6 and B12, therefore makes it possible to obtain the highest squalene yields and productivity.

Method for the Quantification of Squalene in the *Schizochytrium* sp. Biomass

The analysis was carried out by proton NMR at 25° C. after bead disruption of the biomass and cold extraction with chloroform/methanol. The quantification was carried out by means of an internal standard as described below.

The spectra were obtained on an Avance III 400 spectrometer (Bruker Spectrospin), operating at 400 MHz.

Biomass disruption: Precisely weigh out approximately 200 mg of fresh biomass. Add approximately 1-1.5 cm of glass beads and 0.1 ml of methanol. Hermetically seal the tube and stir by means of a vortex mixer for at least 5 min.

Cold extraction: Add approximately 2 mg of triphenyl phosphate (TPP), 0.9 ml of methanol and 2 ml of chloroform. Hermetically seal the tube and stir by means of a vortex mixer for 1 min. Place in a refrigerator. After separation by settling out (minimum of 1 hour), carefully recover the clear upper phase and transfer it into a glass jar for evaporation to dryness, at ambient temperature, under a nitrogen stream. Dissolve the dry extract in 0.5 ml of $CDCl_3$ and 0.1 ml of $CD_3OD$ and transfer into an NMR tube.

Spectrum recording: Perform the acquisition, without solvent suppression, without rotation, with a relaxation time of at least 15 s, after having applied the appropriate settings to the instrument. The spectral window must be at least between −1 and 9 ppm with the spectrum calibrated on the chloroform peak at 7.25 ppm. Use is made of the spectrum after Fourier transformation, phase correction and subtraction of the baseline in manual mode (without exponential multiplication, LB=GB=0).

Making use of the signal: Assign the value 100 to the TPP unresolved peak not containing the chloroform signal between 7.05 and 7.15 ppm (counting as 9 TPP protons). Integrate the area of the squalene signal at 1.55 ppm (singlet counting as 6 protons). Calculation and expression of the results: The results were expressed as crude weight percentage.

$$\text{Content} = \frac{A_s \times P_{TPP}}{6 \times 100} \times \frac{W_{TPP}}{M_{TPP}} \times M_S \times \frac{100}{PE}$$

with
$A_s$: area of the squalene signal at 1.55 ppm
$P_{TPP}$: number of protons of the integrated TPP unresolved peak: 9

$W_{TPP}$: weight, in grams, of TPP weighed out
$M_{TPP}$: molar mass, in grams per mole, of the TPP ($M_{TPP}$=326 g/mol)
$M_S$: molar mass, in grams per mole, of the squalene ($M_S$=410 g/mol)
PE: weight, in grams, of fresh biomass

EXAMPLE 2: STUDY OF THE INFLUENCE OF VITAMINS B1, B6 AND B12

The purpose of the experiment carried out here was to take into account the relative importance of the vitamins in the squalene yields and productivity.

The temperature of the preculture media was defined, as in example 1, at 28° C., and the temperature of the culture/production medium was maintained at 30° C.

Two experiment series were carried out:
addition of vitamins B1, B2 and B6 at the various preculturing and production steps, and
the role of vitamin B12 alone or combined with vitamins B1 and B6. The general culturing conditions were those described in example 1, with, however, a modification with regard to the inoculation with the second preculture which was brought to 2% v/v of the culture.

Table VI brings together the results obtained with the *Schizochytrium* sp strain of the applicant company.

With regard to tests "J" and "K", they demonstrate especially that the addition of vitamin B12 is necessary and sufficient to reach the value of 9 g for 100 g of biomass.

This value even reached 10 g for 100 g of dry biomass when vitamins B6 and B1 were added to the second preculture medium.

It should be noted that the difference between tests "I" and "J" is in terms of the squalene titer: for 9 g of squalene produced for 100 g of dry biomass, the titer was lower in test "J" compared with "I". Vitamins B1 and B6 therefore clearly made it possible to increase the productivity of the system (by increasing the biomass).

EXAMPLE 3: COMPARATIVE TESTS

This experiment was aimed at demonstrating that the operating conditions tested in examples 1 and 2 can also be applied to other microalgae of the type of that held by the applicant company:
*Schizochytrium* sp. referenced ATCC 20888,
*Aurantiochytrium* sp. referenced ATCC PRA 276
The operating conditions were identical to test "I" of example 2.

As a control: a strain conventionally used in the literature for its ability to produce squalene, *Schizochytrium mangrovei*.

TABLE VI

|  | F | G | H | I |
|---|---|---|---|---|
| Vitamins in the 1st preculture (µg/l) | No | B1 + B6 + B12<br>63 000   63 000   350 | B1 + B6 + B12<br>63 000   63 000   350 | B1 + B6 + B12<br>63 000   63 000   350 |
| Vitamins in the 2nd preculture (µg/l) | No | No | B1 + B6 + B12<br>63 000   63 000   350 | B1 + B6 + B12<br>63 000   63 000   350 |
| Vitamins in production (µg/l) | No | No | No | B1 + B6 + B12<br>180 000   180 000   1000 |
| Final titer (g/l) | ND | 0.2 | 3.6 | 6.7 |
| Biomass (g/l) | 35 | 40 | 47 | 76 |
| Squalene to dry biomass (% g/g) | ND | 0.4 | 7.7 | 8.8 |
| Glucose consumed (g/l) | 135 | 138 | 144 | 215 |

|  | J | K |
|---|---|---|
| Vitamins in the 1st preculture (µg/l) | B1 + B6 + B12<br>63 000   63 000   350 | B1 + B6 + B12<br>63 000   63 000   350 |
| Vitamins in the 2nd preculture (µg/l) | B12<br>350 | B1 + B6 + B12<br>63 000   63 000   350 |
| Vitamins in production (µg/l) | B12<br>1000 | B12<br>1000 |
| Final titer (g/l) | 4.9 | 7.4 |
| Biomass (g/l) | 53 | 74 |
| Squalene to dry biomass (% g/g) | 8.9 | 10 |
| Glucose consumed (g/l) | 120 | 220 |

In tests "G", "H" and "I":
For test "G", it is shown that the production of squalene already reached 0.4 g for 100 g of dry biomass, i.e., 4 mg/g of biomass, which is three times the result obtained in the article by C-J Yue and Y. Jiang, *Process Biochemistry*, 2009, 44, 923-927, i.e., with a maximum squalene content of 1.17±0.6 mg/g of *Schizochytrium mangrovei* biomass in the presence of methyl jasmonate.

This result reached even more remarkable values when the provision of vitamins was maintained during the second preculturing (7.7 g for 100 g of dry biomass), and reached a value of close to 9 g for 100 g of dry biomass when this addition of vitamins was carried out again in production.

Table VII gives the results obtained.

TABLE VII

|  | Biomass (g/l) | % squalene (g/g) | Squalene titer (g/l) |
|---|---|---|---|
| I | 76 | 8.8 | 6.7 |
| *Schizochytrium* sp. ATCC 20888 | 60 | 6.2 | 3.7 |
| *Aurantiochytrium* sp. ATCC PRA 276 | 72 | 2.3 | 1.7 |
| *Schizochytrium mangrovei* | 82 | 0.3 | 0.2 |

The squalene production was greater than 2 g per 100 g of biomass for all the *Thraustochytriales* of the subfamily sp. tested. That of *S. mangrovei* complies with what is described in the literature (for the best results obtained): 2 mg of squalene/g of dry biomass.

EXAMPLE 4: OBTAINING THE CRUDE OIL RICH IN SQUALENE PRODUCED BY FERMENTATION

The biomass obtained at the end of example 1 (test "E") was at a concentration of 54 g/l at the end of fermentation.

The squalene titer obtained at the end of fermentation was 4.4 g/l.

The biomass was removed from the fermenter and then concentrated by centrifugation to 120 g/l.

The biomass was kept stirring at 150 rpm in a 50 l tank, and heated to 60° C.

The pH was then adjusted to 10 with 45% potassium hydroxide.

These conditions were maintained for 6 h in order to achieve complete alkaline lysis.

The quality of the lysis was monitored under an optical microscope and by sample centrifugation (2 min, 10,000 g).

At the end of lysis, 10 liters of ethanol (1 volume of ethanol/volume of lysate) were added to the tank maintained at 45° C. and stirred for 10 min.

10 liters of hexane were then added to the tank kept stirring for 30 min.

The mixture was then centrifuged in order to separate the light fraction (hexane+oil) which was stored in a 1 m$^3$ tank.

The heavy (aqueous) phase was again brought together with 10 liters of hexane so as to perform a second extraction according to the same scheme as previously in order to increase the extraction yield.

The two organic fractions were combined in order to carry out the evaporation of the hexane in a rotary evaporator.

The hexane residues of the oil extracted were removed by evaporation in a wiped film evaporator (80° C.; 1 mbar).

The crude oil was thus recovered with a yield of 70%.

The invention claimed is:

1. A process for the producing squalene from microalgae belonging to the *Thraustochytriales* family, comprising:
   culturing *Schizochytrium* sp. CNCM I-4469 in at least one of a preculture medium and a culture medium,
   adding a vitamin mixture comprising from about 1 to about 1000 μg of vitamin B 12, 0.1 mg to 200 mg of vitamin B 1, and 0.1 mg to 200 mg of vitamin B6 to at least one of said preculture medium and said culture medium,
   conducting said culturing in said at least one of said preculture medium and said culture medium at a temperature of between 25° C. and 35° C. in at least one of said preculture and culture medium containing said vitamin mixture occurring at 28° C., and, recovering biomass containing at least 2 g of squalene for 100 g of dry biomass.

2. The process of claim 1, wherein said culturing of the microalgae comprises:
   first, preculturing said microalgae for 24 to 36 hours in Erlenmeyer flasks, at a temperature of 28° C., from an isolated colony on an agar dish,
   second, preculturing for 24 to 36 hours in Erlenmeyer flasks, at a temperature of 28° C., with an inoculum of 1% (v/v) resulting from the first preculturing, and
   third, culturing for 60 to 150 hours at 30° C., in a fermenter regulated to provide an oxygen transfer of at most 45 mmol/l/hour, with an inoculum of 0.5% to 2% (v/v) resulting from the second preculturing.

3. The process of claim 2, wherein the total content of vitamin B 12 in first and second preculturing is between 1 and 10 μg/l.

4. The process of claim 2, wherein the total content of vitamins B 1 and B 6 during the first and second preculturing steps is between 100 and 200 μg/l.

5. The process of claim 2, wherein the total content of vitamin B 12 during the first and second preculturing steps is between 1 and 10 μg/l of culture medium, and
   the total content of vitamin B 12 at the beginning of the third culturing is about 1000 μg/l of culture medium.

6. The process of claim 5, wherein the total content of vitamins B 1 and B6 during the first and second preculturing is between 100 and 200 μg/l of culture medium, and the total content of vitamins B 1 and B6 at the beginning of the third culturing is between 150 and 200 mg/l of culture medium.

7. The method of claim 1, wherein said recovering squalene comprises recovering the microalgae from said culture medium, rupturing said microalgae and extracting squalene from said ruptured microalgae.

8. A process for production of squalene in microalgae comprising,
   a) culturing *Schizochytrium* sp. CNCM I-4469 in at least one of a preculture medium or culture medium containing a vitamin mixture, at a temperature of between about 28° C. and 35° C., at least one of said preculture medium or culture medium containing a vitamin mixture, said vitamin mixture containing per liter of said preculture or culture medium,
      1) 1 to 1000 μg of vitamin B 12,
      2) 0.1 mg to 200 mg of vitamin B 1, and
      3) 0.1 mg to 200 mg of vitamin B6, and
   b) recovering squalene from the culturing, wherein the amount of squalene produced and recovered is greater than or equal to 2 g squalene for 100 g dry biomass.

9. A process for producing squalene from microalgae, comprising,
   a) culturing *Schizochytrium* sp. CNCM I-4469, in at least one of a preculture phase and a culture phase,
   b) using in at least one of said preculture phase and said culture phase a culture medium containing a vitamin mixture, said vitamin mixture containing per liter of culture medium, 1 to 1000 μg of vitamin B 12, 0.1 mg to 200 mg of vitamin B 1, and 0.1 mg to 200 mg of vitamin B6,
   c) conducting said culturing at a temperature of between 25° C. and 35° C., and at least one said preculture and culture phases at a temperature between 28° C. and 35° C., and
   d) recovering squalene.

10. The process of claim 9, wherein said culturing comprises a preculturing phase and a culturing phase, and said preculturing phase comprises first and second preculturing phases, each conducted for 24 to 36 hours at a temperature of 28° C.

11. The process of claim 10, wherein said culturing phase is conducted for 60 to 150 hours at 30° C.

12. The process of claim 9, wherein the squalene recovered is between 0.5 g/l to 8.2 g/l.

* * * * *

UNITED STATES PATENT AND TRADEMARK OFFICE
CERTIFICATE OF CORRECTION

PATENT NO. : 10,087,467 B2
APPLICATION NO. : 14/118641
DATED : October 2, 2018
INVENTOR(S) : Bernard Pora et al.

It is certified that error appears in the above-identified patent and that said Letters Patent is hereby corrected as shown below:

On the Title Page

(73) Assignee name should read as follows:
--Roquette Freres, Lestrem (FR)--

Signed and Sealed this
Twenty-fifth Day of December, 2018

Andrei Iancu
*Director of the United States Patent and Trademark Office*